United States Patent [19]

Dance

[11] Patent Number: 5,117,839
[45] Date of Patent: Jun. 2, 1992

[54] EXCHANGEABLE FIXED WIRE CATHETER

[75] Inventor: Creg W. Dance, Elk River, Minn.

[73] Assignee: Lake Region Manufacturing Co., Inc., Chaska, Minn.

[21] Appl. No.: 584,461

[22] Filed: Sep. 18, 1990

[51] Int. Cl.⁵ ............................................... A61B 5/00
[52] U.S. Cl. .................................... 128/772; 128/657; 604/165
[58] Field of Search ................. 128/657, 772; 604/95, 604/164, 165

[56] References Cited

U.S. PATENT DOCUMENTS

| | | | |
|---|---|---|---|
| 4,646,747 | 3/1987 | Packard et al. | 128/344 |
| 4,650,466 | 3/1987 | Luther | 128/348 |
| 4,664,113 | 5/1987 | Frisbie et al. | 128/344 |
| 4,748,982 | 6/1988 | Horzewski et al. | 128/344 |
| 4,748,984 | 6/1988 | Patel | 128/344 |
| 4,808,164 | 2/1989 | Hess | 604/95 |
| 4,838,269 | 6/1989 | Robinson et al. | 128/344 |
| 4,844,092 | 7/1989 | Rydell et al. | 128/772 |
| 4,846,174 | 7/1989 | Willard et al. | 128/344 |
| 4,957,117 | 9/1990 | Wysham | 128/772 |

*Primary Examiner*—Max Hindenburg
*Attorney, Agent, or Firm*—Hugh D. Jaeger

[57] ABSTRACT

An apparatus providing the benefits of a catheter with a fixed guidewire, while retaining the advantages of a catheter with an adjustable, removable, and exchangeable guidewire. The catheter may be designed for use in the urinary tract, cardiovascular system, or other body passages. The guidewire is advanced through the catheter from the proximal to the distal end for the required distance. This may be sufficient to make the catheter and the guidewire coextensive or to make either the catheter or guidewire protrude from the distal end, as desired. The guidewire may be secured to the proximal end of the catheter by rotation of a compressible fixation device. The connection is frictionally sealed. The guidewire may be rotated with respect to the catheter in the same manner as with a fixed wire catheter. Opposite rotation of the compressible fixation device frees the guidewire for removal, advancement or exchange.

10 Claims, 5 Drawing Sheets

EXCHANGEABLE FIXED WIRE CATHETER

BACKGROUND OF THE INVENTION

1. Field of the Invention

The present invention relates generally to catheters utilizing guidewires, and more particularly, relates to catheters with proximal connectors facilitating the movement of guidewires.

2. Description of the Prior Art

Catheters for insertion into the body have been known in the medical arts for many years. These may be used for diagnostic purposes, such as in various radiology applications, or may be used therapeutically, as in angioplasty and atherectomy procedures. U.S. Pat. No. 4,808,164 issued to Hess describes a multipurpose catheter. U.S. Pat. No. 4,650,466 issued to Luther and U.S. Pat. No. 4,748,984 issued to Patel describe catheters designed for use in atherectomy procedures.

A key feature in the clinical use of a catheter is the ability of the attending physician to steer the distal end of the catheter through the body to the desired diagnostic or treatment site. To accomplish this end, catheter manufacturers have employed a number of techniques. One of the most common approaches is through the use of a guidewire which is often employed in an internal lumen of the catheter. The references discussed above all teach the use of a guidewire with the catheter disclosed.

A number of catheter designs have employed fixed guidewires. The chief advantage of this approach is the steerability afforded by combined and independent rotation of the guidewire and the sealing of the lumen in which the guidewire is located. This also promotes a low profile. The prime disadvantages of the fixed guidewire catheter include inability to adjust the length of the guidewire in relation to the length of the catheter and to remove the guidewire to free the lumen for other purposes. U.S. Pat. No. 4,664,113 issued to Frisbie shows a typical fixed guidewire catheter design.

Because of the disadvantages with fixed guidewire systems, many current catheter systems employ removable guidewires. U.S. Pat. No. 4,748,982 issued to Horzewski, et al. discusses a balloon angioplasty catheter with a totally removable guidewire. However, the guidewire lumen of the Horzewski, et al. device is not sealed.

U.S. Pat. No. 4,646,742 issued to Packard, et al. and U.S. Pat. No. 4,846,174 issued to Willard, et al. also teach catheters with removable guidewires. These devices employ a seal on the proximal end of the catheter for purposes of sealing an internal thru-lumen. These devices, however, fail to provide for the rotation of the guidewire without the attachment of an independent rotation knob to the proximal end of the guidewire.

A major improvement to catheter systems having removable guidewires is the ability to seal the guidewire lumen. U.S. Pat. No. 4,838,269 issued to Robinson shows the use of an O-ring to seal the proximal end of the guidewire lumen. However, the Robinson catheter yet has the key disadvantage of the difficulty in rotation of the guidewire combined with the independence of rotation of the catheter.

SUMMARY OF THE INVENTION

The present invention provides a catheter system with a removable guidewire. As such, the relative lengths of the guidewire and the catheter may be readily adjusted. Furthermore, the guidewire is completely removable to permit use of the guidewire lumen for a different purpose or to provide for insertion of another guidewire having different handling characteristics.

The guidewire lumen is frictionally sealed against the guidewire by a unique compression seal. This seal is conical rather than O-ring shaped as in the prior art to increase the active surface area of the seal.

A compressible fixation device is used to frictionally engage the guidewire against longitudinal movement with respect to the catheter. Rotation of this compressible fixation device "fixes" the length of the guidewire causing the catheter to handle as if it had a fixed guidewire. Counter rotation of the compressible fixation device unlocks the guidewire permitting longitudinal movement and removal if desired.

A rotational surface distal to the compressible fixation device, but proximal to the guidewire lumen seal, facilitates independent rotation of the guidewire. When the guidewire is "fixed" by the compressible fixation device, rotation of the catheter/guidewire combination is also readily accomplished.

A significant advantage of the guidewire and catheter interface using the present invention is the combination of a proximal connector that facilitates the guidewire rotation, guidewire removal and guidewire replacement with appropriate sealing of internal catheter lumens, and the adjustment and fixation of the guidewire to the catheter while providing for independent rotation of both catheter and guidewire with the internal catheter lumens having an appropriate sealing mechanism.

The present invention provides the guidewire and catheter combination with the following features catheter inner lumen seal, independent rotation of guidewire and catheter, guidewire fixation, and guidewire length adjustment.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
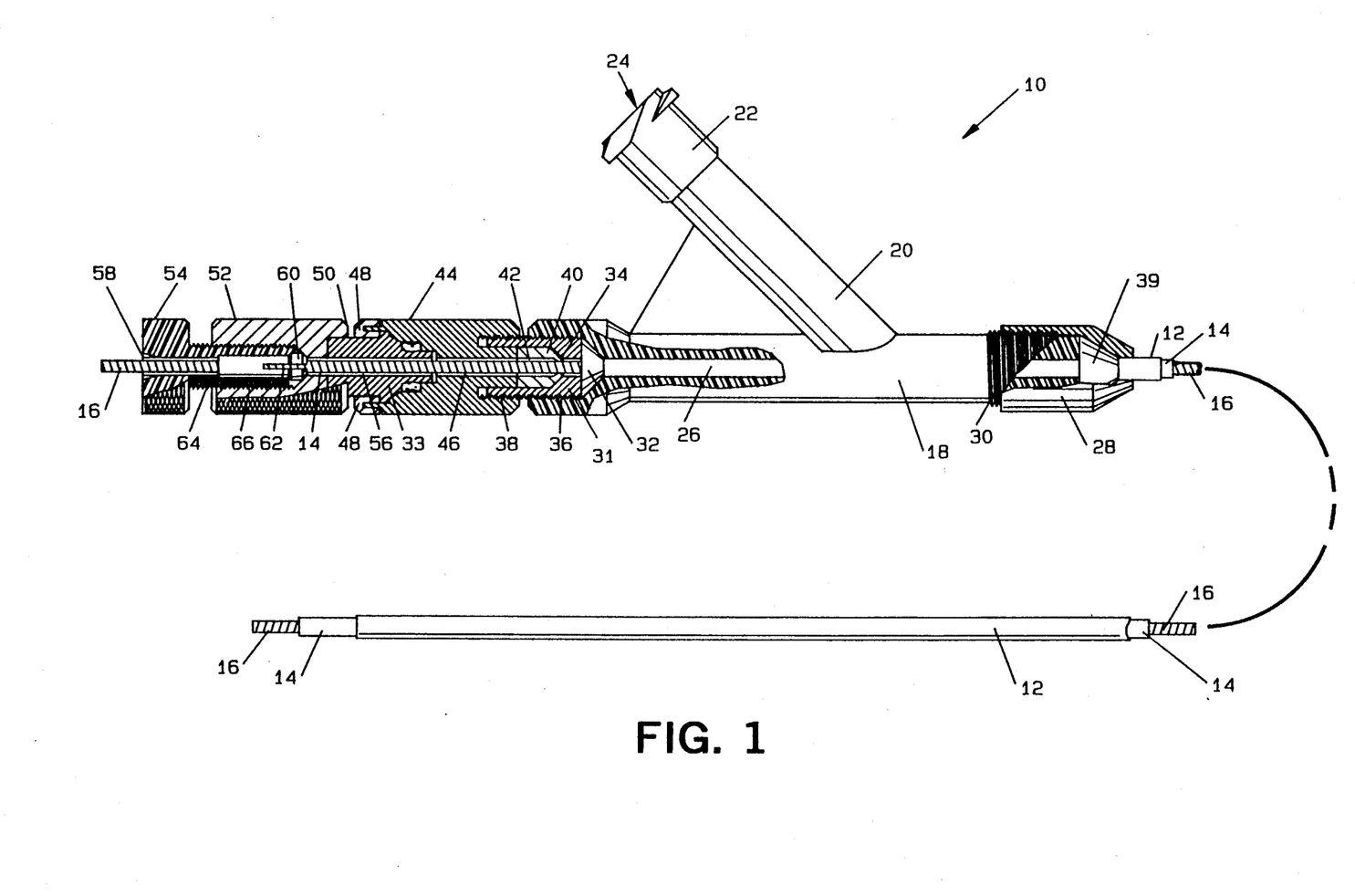
FIG. 1 is a plan view in partial cutaway of a catheter system employing the present invention.

FIG. 1 shows a catheter system 10 employing t he present invention which provides the handling advantages of both fixed and removable guidewire catheter systems. In the preferred mode, catheter body 12 is a flexible tube of conventional construction shown by way of example and not by way of limitation is a catheter of coaxial construction. However, catheter body 12 may also be a spring coil with or without sheath or other structure defining a lumen for passage of a guidewire. It may be designed with a number of therapeutic features at its distal end including an atherectomy device, a dilatation balloon, etc. No such feature is shown for clarity. Inner sheath 14 is shown extending from the distal end of catheter body 12. Guidewire 16 also extends from the distal end of catheter body 12.

Guidewire 16 is preferably of a coiled construction. Stainless steel is a preferred material; however, other material and configurations are also acceptable. Guidewire 16 will normally extend from the proximal end of catheter system 10, as shown, and may extend from the distal end as well depending upon the application and the desired handling characteristics.

Catheter body 12 may be of a single lumen, multiple lumen or coaxial design. A coaxial lumen catheter is shown by way of example. However, the present invention is not limited to this configuration.

In the coaxial lumen system, the proximal end of catheter body 12 is flared and terminates at conical point 39. In this way, sealing fluid communication is established between the outer lumen and secondary branch 20 of wye 18.

The proximal end of the inner sheath 14 proceeds through lumen 26 of wye 18 and is flared and terminates at conical point 32. Lumen 26 extends distally through the main branch of wye 18. Wye 18 is preferably molded of a rigid plastic. Secondary branch 20 of wye 18 terminates in hub 22 having aperture 24. Secondary branch 20 may be coupled to an infusion source, power source, or pressurized fluid source, depending upon the application. The outer lumen of catheter body 12 is sealed against wye 18 at conical point 39 and the inner lumen 26 is sealed at conical point 32 as further explained below. Strain relief attachment is provided by rigid threaded nut 28, which is attached to the distal end of wye 18 by screwing onto threads 30.

Major components needed to practice the present invention include double male threaded adapter 31, device attachment nut 44, double male barrel 33, knurled guidewire rotation knob 52, and knurled guidewire fixation knob 54, which are all preferably fabricated of plastic, aluminum or other strong but light material. These components may be manufactured separately and simply attached to a catheter assembly or made an integral part of wye 18.

Double male threaded adapter 31 is made with the appropriate threads to attach to threads 36 of wye 18 as shown, as such different thread configurations or even female threads may be needed for some applications. Device attachment nut 44 is attached to double male threaded adapter 31 and hence wye 18 by threads 38. Proper attachment ensures that inner lumen 26 and lumen 46 of device attachment nut 44 are directly aligned. Also compressible seal 34 must frictionally engage the guidewire 16. Threaded adapter 31 sealingly engages against conical point 32 and the flared proximal end of inner catheter 14. Both of these requirements are greatly facilitated by a semiflexible seal 40 having a lumen 42, which bends to accommodate slight differences in longitudinal and axial alignment.

Double male barrel 33 aligns knurled guidewire rotation knob 52 with device attachment nut 44 and provides for relative rotation at the intersection of edges 48 and 50. With guidewire 16 fixed as described in more detail below, rotation of knurled guidewire rotation knob 52 independent of wye 18 (and device attachment nut 44) causes rotation of guidewire 16 independent of catheter body 12.

Knurled guidewire fixation knob 54 has male threads 64 which are screwed into female threads 66 of knurled guidewire rotation knob 52. This aligns lumens 56 and 62 with lumen 46. As knurled guidewire fixation knob 54 is tightened, compressible fixation device 60 frictionally engages guidewire 16 causing it to handle as if it were a fixed guidewire. The excess length of guidewire 16 extends through aperture 58 as shown.

Figure 2:
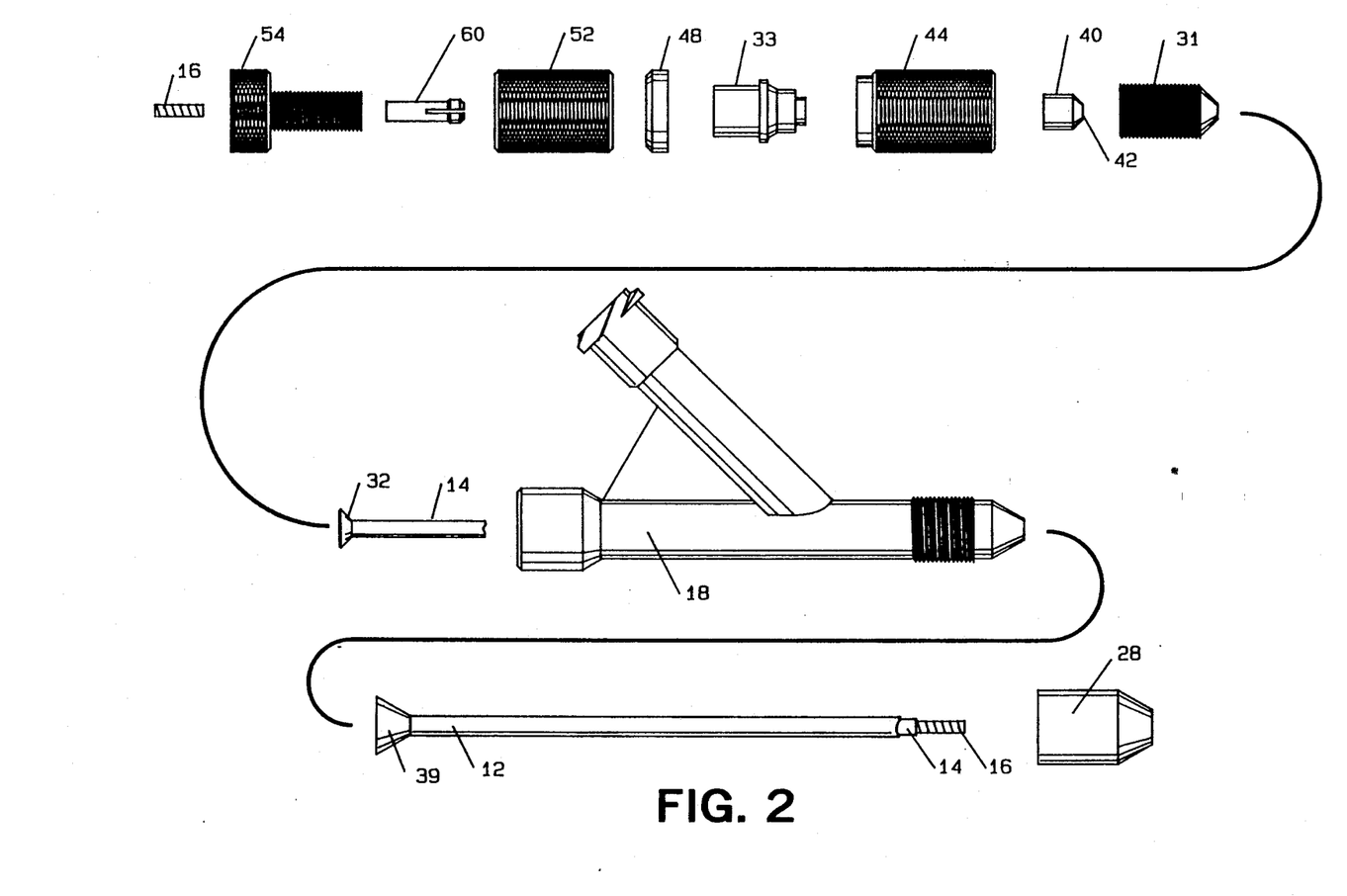
FIG. 2 is an exploded view of the catheter system.

FIG. 2 is an exploded view of the catheter 10 wherein like parts are referenced as previously described.

Figure 3:
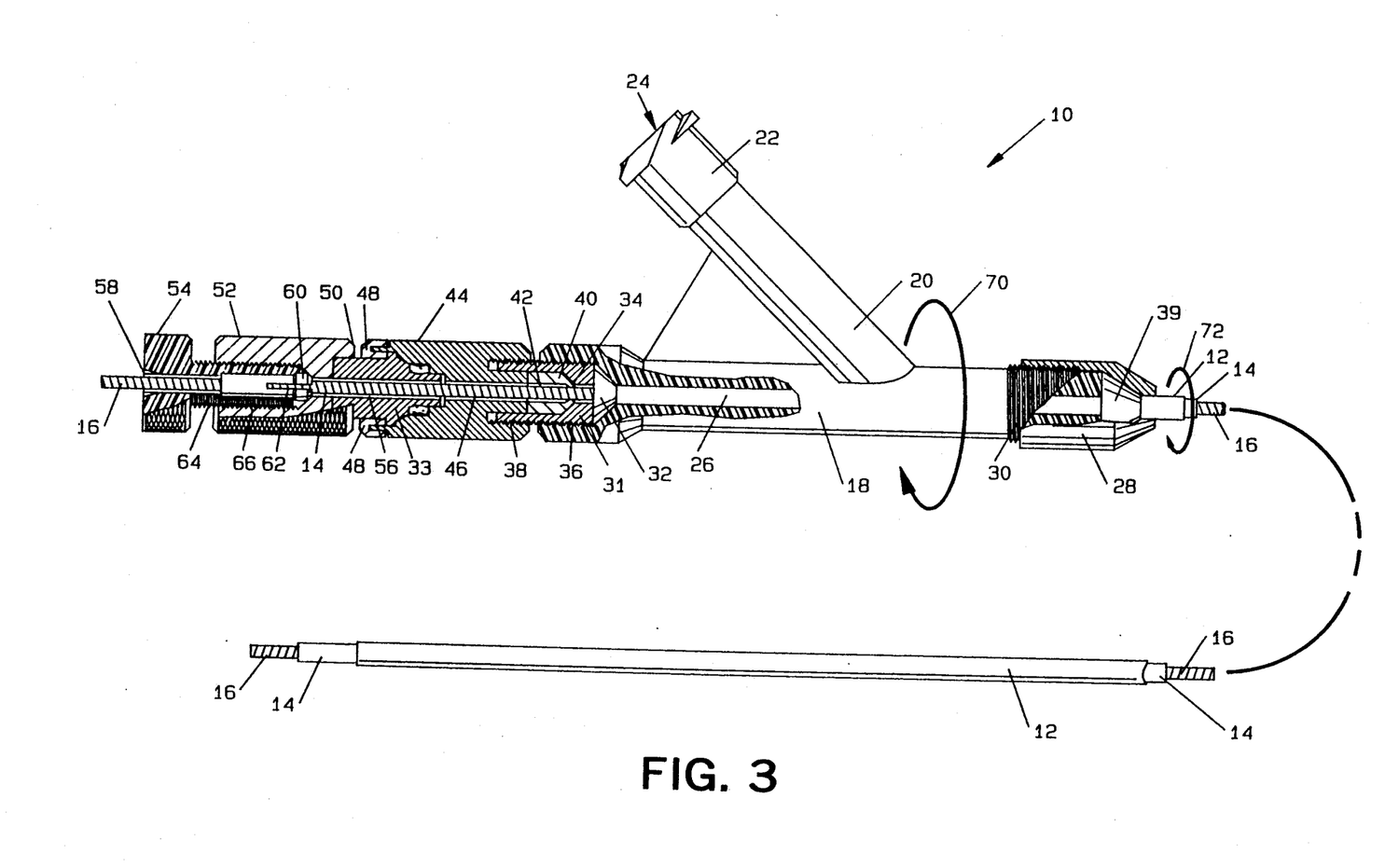
FIG. 3 is a conceptual view of the catheter system showing rotation of the catheter/guidewire combination.

FIG. 3 is a conceptual view of catheter system 10 showing operation as a fixed wire catheter system. In this mode, knurled guidewire fixation knob 54 has been tightened such that guidewire 16 is frictionally engaged in the position shown. Rotation of wye 18, as shown by arrow 70, causes rotation of the entire catheter system 10 to include both catheter body 12 and guidewire 16 as shown by arrow 72.

Figure 4:
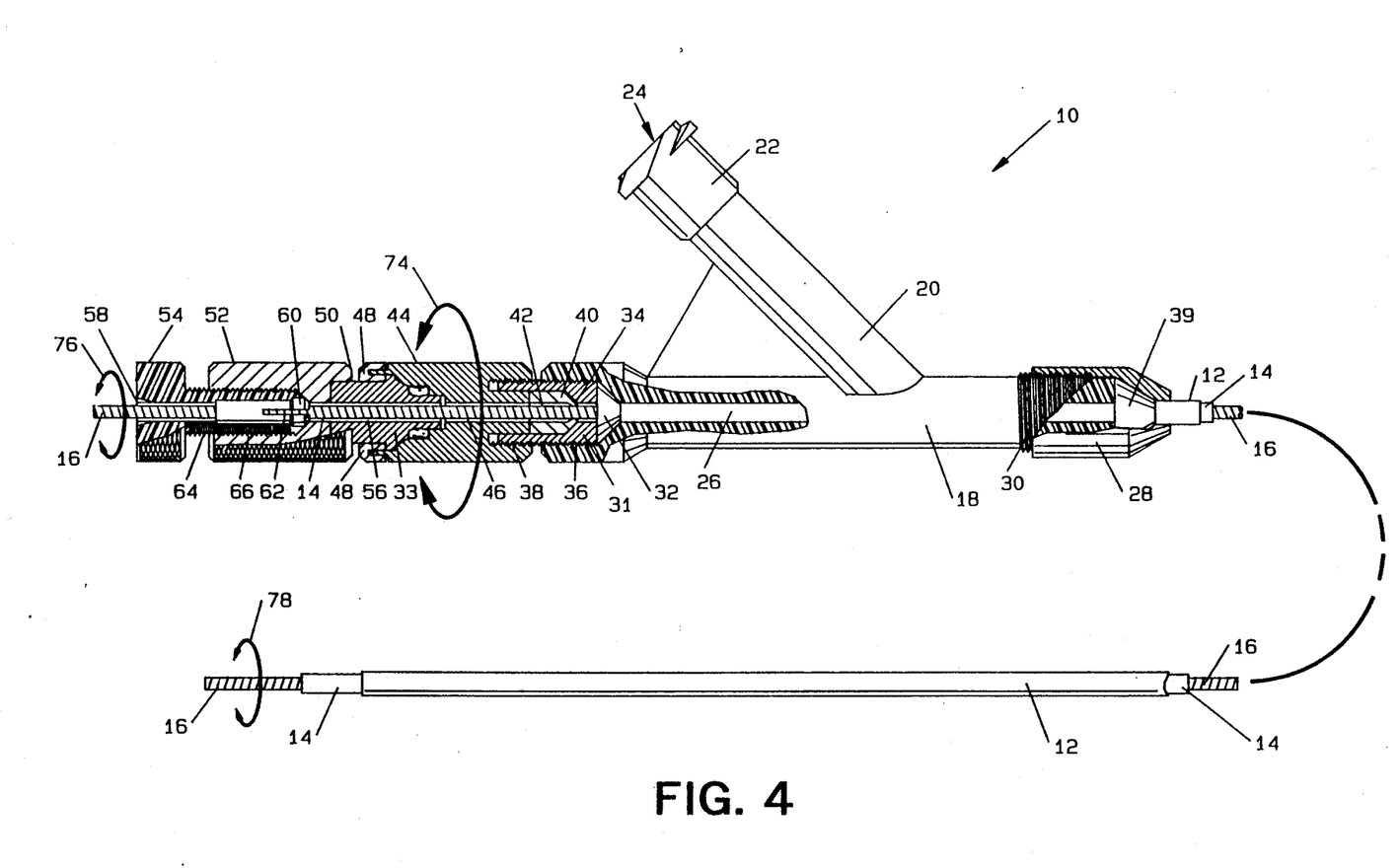
FIG. 4 is a conceptual view of the catheter system showing independent rotation of the guidewire; and, FIG. 5 is a conceptual view of the catheter system showing counter rotation of the collet to permit longitudinal movement and/or removal of the guidewire.

FIG. 4 is a conceptual view of catheter system 10 showing independent rotation of guidewire 16. Again guidewire 16 is frictionally engaged by rotation of knurled guidewire fixation knob 54. As wye 18 is held stationary and knurled guidewire rotation knob 52 is rotated in the direction shown by arrow 74, catheter body 12 remains stationary while guidewire 16 is rotated as shown by arrows 76 and 78. This is helpful in positioning the distal end of catheter body 12 when guidewire 16 and catheter body 12 are differentially bent to steer into difficult areas.

Figure 5:
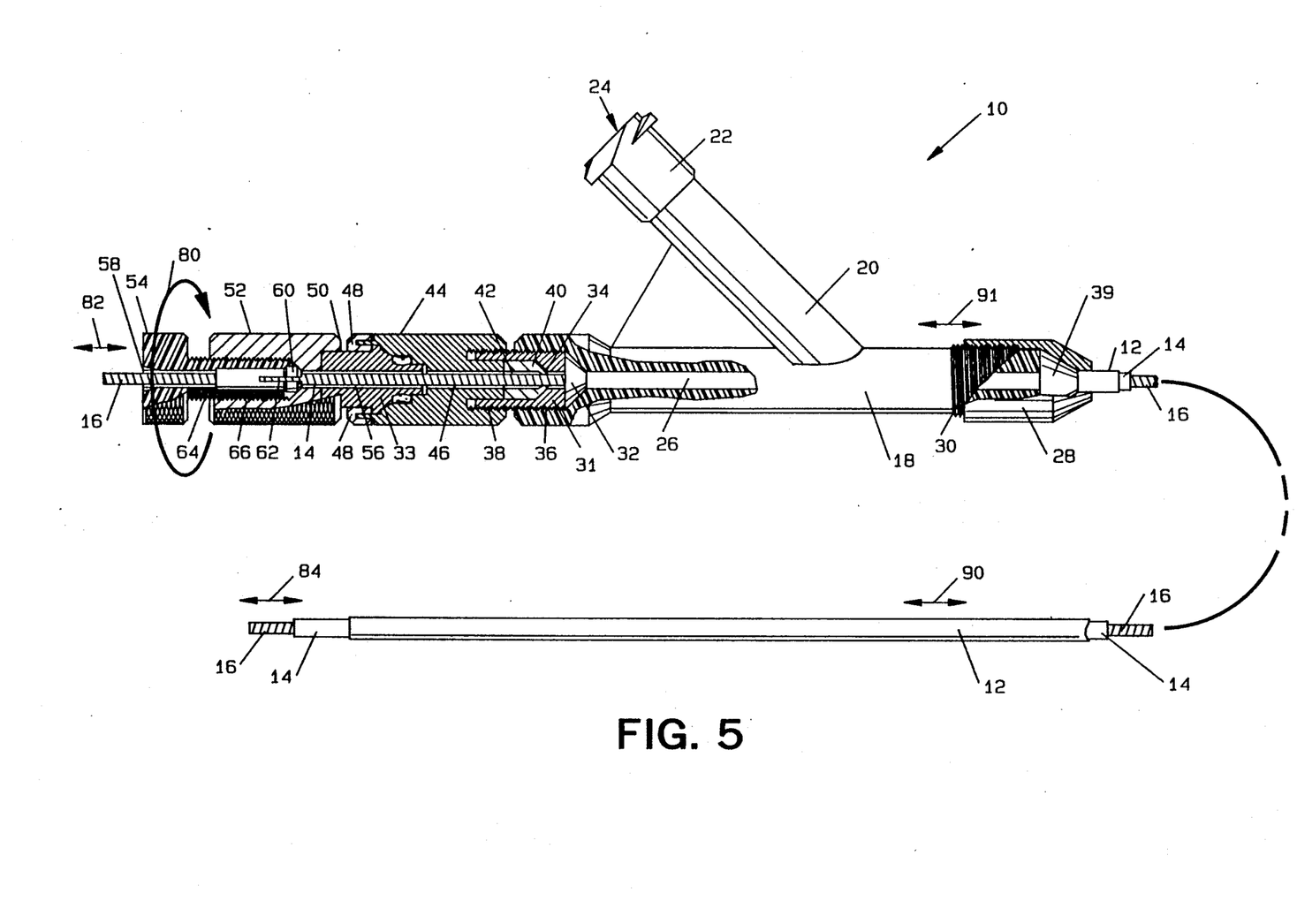

FIG. 5 is a conceptual view of catheter system 10 showing movement guidewire 16 longitudinally. In this mode, knurled guidewire fixation knob 54 is rotated in the direction of arrow 80. This releases the frictional engagement of guidewire 16 by compressible fixation device 60 (see also FIG. 1). The disengagement permits longitudinal movement of guidewire 16 with respect to catheter body 12 and wye 18 as shown by arrows 82 and 84. In this manner, guidewire 16 may be repositioned, removed, or replaced as desired by the attending physician. Conversely, guidewire 16 may be held fixed and the catheter assembly may be removed, repositioned, or rotated independently of guidewire 16 as shown by arrows 90 and 91.

Having thus described the preferred embodiments o the present invention, those of skill in the art will be readily able to apply the teachings found herein to other embodiments within the scope of the claims hereto attached.

We claim:

1. An apparatus comprising:
   a. a catheter body having a proximal end and a distal end;
   b. a guidewire having a proximal end and a distal end moveably located within said catheter body;
   c. releasably engaging means attached to said guidewire proximal end for releasably engaging said guidewire against longitudinal movement with respect to said catheter body, said releasably engaging means comprising compressible fixation means for fixing the position of said guidewire in said catheter body upon compression thereof, ad compression means associated with said compressible fixation means for compressing said compressible fixation means; and d. rotating means attached to said guidewire for rotating said guidewire with respect to said catheter body.

2. An apparatus according to claim 1 further comprising means attached to said releasably engaging means for sealing said guidewire to said catheter body.

3. An apparatus according to claim 2 wherein said compression means comprises a knurled fixation knob.

4. An apparatus according to claim 3 wherein said rotating means further comprises a knurled rotation knob.

5. The apparatus of claim 1, wherein said compressible fixation means comprises a substantially cylindrical member having a proximal end and a distal end, said substantially cylindrical member having a central lumen through which said guidewire passes, and a slit extending from said distal end and terminating before said proximal end so that upon compression of said distal end, said distal end frictionally engages said guidewire.

6. The apparatus of claim 5, wherein said compression means comprises a fixation knob having a distal end and a promixal end, and a central lumen through which said guidewire passes and in which said compressible fixation means is disposed.

7. The apparatus of claim 6, wherein the outer diameter of said distal end of said substantially cylindrical member is greater than the outer diameter of said proximal end.

8. The apparatus of claim 8, wherein said means attached to said guidewire for rotating said guidewire with respect to said catheter body comprises a rotation knob having a proximal end and a distal end and a central lumen through which said guidewire passes; said central lumen having a central portion of diameter slightly larger than the outer diameter of said guidewire, and a proximal end portion of larger diameter than said central portion; and wherein the distal end of said fixation knob is disposed in said proximal end portion.

9. The apparatus of claim 6, wherein said proximal end portion of larger diameter of said rotation knob includes thread for engaging said distal end of said fixation knob.

10. The apparatus of claim 9, wherein said central lumen of said rotation knob has a distal end portion of diameter larger than said central portion diameter, said distal end portion rotatably engaging a double male barrel member having a central lumen through which said guidewire passes.

* * * * *

UNITED STATES PATENT AND TRADEMARK OFFICE
CERTIFICATE OF CORRECTION

PATENT NO. : 5,117,839
DATED : June 2, 1992
INVENTOR(S) : Creg W. Dance

It is certified that error appears in the above-indentified patent and that said Letters Patent is hereby corrected as shown below:

Column 4, lines 59 and 60, that portion of claim 1 reading:
c. "releasably engaging means attached to said guidewire proximal end"
should read:
c. --releasably engaging means attached to said catheter body--

Column 5, line 1, that portion of claim 1 reading:
d. "rotating means attached to said guidewire"
should read:
d. --rotating means attached to said catheter body--

Signed and Sealed this

Third Day of October, 1995

Attest:

BRUCE LEHMAN

*Attesting Officer*     *Commissioner of Patents and Trademarks*

Adverse Decision In Interference

Patent No. 5,117,839, Creg W. Dance, EXCHANGEABLE FIXED WIRE CATHETER, Interference No. 103,379, final judgment adverse to the patentee rendered June 20, 2000, as to claims 1-4 and 8.

*(Official Gazette April 30, 2002)*